United States Patent
Osaka et al.

(10) Patent No.: US 6,544,288 B2
(45) Date of Patent: *Apr. 8, 2003

(54) BIOCOMPATIBLE TITANIUM IMPLANT FOR MEDICAL USE

(75) Inventors: Akiyoshi Osaka, 416-1, Ohdara-cho, Okayama-shi, Okayama (JP); Satoshi Hayakawa, Okayama (JP); Kanji Tsuru, Okayama (JP); Keiko Koyano, Kurashiki (JP); Keizo Ohta, Okayama (JP)

(73) Assignees: Akiyoshi Osaka, Okayama (JP); Ohta, Inc., Okayama (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/528,280

(22) Filed: Mar. 17, 2000

(65) Prior Publication Data
US 2002/0143398 A1 Oct. 3, 2002

(30) Foreign Application Priority Data

Mar. 19, 1999 (JP) ............................................. 11-076653

(51) Int. Cl.[7] .................................................. A61F 2/02
(52) U.S. Cl. ..................................... 623/11.11; 424/423
(58) Field of Search ............................... 427/2.27, 2.24, 427/2.1, 2.26; 600/397; 424/422, 423; 606/76; 623/11.11, 23.53, 23.57, 24, 25, 920, 923, 23.6; 204/450

(56) References Cited

U.S. PATENT DOCUMENTS

| | | | | |
|---|---|---|---|---|
| 4,818,572 A | * | 4/1989 | Shimamune et al. | 427/327 |
| 5,310,464 A | * | 5/1994 | Redepenning | 204/180.2 |
| 5,855,612 A | * | 1/1999 | Ohtuki et al. | 623/11 |
| 6,190,407 B1 | * | 2/2001 | Ogle et al. | 623/1.51 |

* cited by examiner

Primary Examiner—David J. Isabella
Assistant Examiner—Urmi Chattopadhyay
(74) Attorney, Agent, or Firm—Koda & Androlia

(57) ABSTRACT

A biocompatible implant for medical use having a layer of titanium or titanium alloys on its surface. The implant is electrochemically treated by using it for an anode in an electrolyte solution containing calcium ions so as to produce a layer of hydrated oxides or hydrated oxide gels, or is subject to an anodic treatment. Subsequently the implant is subject to another electrochemical surface treatment where the implant is employed as a cathode so as to yield a layer that involves or is adsorbed with calcium ions, thus forming on the implant a hydrated gel layer that has an excellent ability of forming apatite.

5 Claims, 6 Drawing Sheets

○ : apatite
△ : calcite
▲ : vaterite
□ : Ca(OH)$_2$
■ : titanium

BIOCOMPATIBLE TITANIUM IMPLANT FOR MEDICAL USE

BACKGROUND OF THE INVENTION

1. Field of Invention

The present invention is concerned with implant materials for medical use that have a highly biocompatible surface layer of titanium or titanium alloys. More specifically, the implant materials have high biocompatibility or bioactivity due to appropriate electrochemical treatments on their surfaces.

2. Prior Art

The implant materials having titanium or titanium alloys as their surface layer exhibit so little biocompatibility or bioactivity that they are confronted with a great problem of displacement or loosening unless they are provided with those properties.

One of the attempts against such problem is to develop a group of implants hat are coated with a layer of calcium phosphate comics such as hydroxy apatite due to plasma spraying or coated with an apatite layer due to dipping the materials in a multicomponent solution containing calcium ions and phosphate ions as the major ingredients, followed by calcining. However, some shortcomings are found in those surface modification treatments: The former method of plasma spraying needs temperatures higher than 1000° C. and a much more expensive apparatus as well as a more complicated procedure; the latter method of dip-coating not only requires a longer period of treatments but attains insufficient adhesion between the implant metal surface and the as-deposited coating. As a result, it exhibits only inferior fixation bonds to living tissues.

Thus a method of providing direct fixation between the metal surface and living :tissues has been developed where titanium or titanium alloy substrates or those having those metals as the surface layer are soaked in a highly concentrated alkaline solution to yield a hydrated gel layer, which layer can deposit apatite when it is placed under body environment after calcination at a higher temperatures. An example is described in Japanese Patent Application Laid-Open No. Hei 1-275766. This method, however, embodies some drawbacks in the procedure like danger of using a highly concentrated alkaline solution as well as unexpected distortion of shape and damage in mechanical properties due to heating up to as high as 600° C. Such treatment raises the cost of the implants.

Another method of promoting strong fixation of the titanium or titanium alloy implants has been proposed where the implants are soaked in a warm aqueous solution of hydrogen peroxide containing some metal ions to yield a hydrated titania gel layer that involves those metal ions hence exhibits an improved ability of depositing apatite when soaked in a body fluid or simulated body fluid with calcium and phosphate ions as the major ingredients. The present inventors studied the processes and disclosed such a method of highly efficient and improved treatment in Japanese Patent No. 2795824.

SUMMARY OF THE INVENTION

Accordingly, the object of the present invention is to provide the surface of metallic substrates with high bioactivity by virtue of a more simple method and treatment at temperatures lower than the method of soaking the in such aqueous hydrogen peroxide solutions described above. The present inventors have further studied so that they could provide metallic materials having mechanical strength enough for implants, excellent bonding to living tissues, and superior fixation.

The present invention then is to provide the titanium and titanium alloy substrate with bioactivity due to electrochemical treatments as the solution for the problems in the prior art. That is, either titanium or titanium alloys or materials having those as their surface layer are employed as the cathode and electrolyzed in calcium ion-containing aqueous solutions, through which treatment the substrates are covered with a layer with calcium ion absorbed or involved.

Another invention is concerned either with such titanium or titanium alloys or materials with those as their surface layer that are first electrochemically treated in a calcium ion-containing aqueous solution employing those as the anode to yield an oxide hydrated layer on titanium or titanium alloys (the layer is to be simply denoted as a hydrated oxide layer, and sometimes is present in the form of a hydrated gel layer) before those metallic materials are subject to cathodic polarization (cathodic treatment) so that the cathodic treatment ensures absorption or involvement of calcium ions in the hydrated oxide layer. Such consecutive anodic and cathodic treatments hence yield biomedical implant materials exhibiting both excellent bioactivity and outstanding compatibility to living tissues by virtue of the hydrated oxide gel layer having superior ability of spontaneously depositing apatite layer under body environment.

The medical implant materials concerned with the present invention, then, hold calcium ions inside or on the hydrated oxide layer due to changing the polarity of the electrode made of the implant materials from anode to cathode. The state of the calcium ions is held either being absorbed or being involved. Appropriate cathodic potential applied to the cathode made of the titanium or titanium alloy implants may be rarer(more negative) than $-0.5$ V vs. the Ag/AgCl reference electrode. The potential is hereafter expressed by the value in volts vs. Ag/AgCl electrode unless otherwise described. Favorable effects are obtained for the potentials $-1.5$ to $-3$ V. The potential rarer than or exceeding $-3$ V leads to rigorous electrolysis of water and violent evolution of oxygen or hydrogen gas at each electrode hence is inadequate. Appropriate anodic potentials may be larger than $+0.5$ V. Although a higher anodic potential gives rise to a thicker hydrated oxide layer the potentials of $+1.5$ V or greater are most favorable for the sake of stronger adhesion among the implant, the hydrated oxide layer, and the apatite layer deposited under body environment.

The implants suitable for the treatment in the present invention can be a wide range of natural or artificial organic polymers and metallic materials, and are not restricted in any means. Most favorably chosen polymer materials are such single component natural or artificial polymers or multicomponent composites consisting of a few of them that are mechanically strong and tough enough to be employed as implant materials for medical use. The polymers of special preference include polyethylene, polypropylene, polytetrafluoroethylene (Teflon®, Goretex®), polyvinylchloride, and polycarbonate, to name a few. For attaining bioactivity those organic polymer materials should be provided with a surface layer of titanium or titanium alloys due to some surface modification procedure. Several methods can be employed for the surface modification such as plating, spraying, ion injection, PVD, CVD, ion mixing, and other common methods.

The metallic substrates suitable for the treatment of the present invention are not only titanium or titanium alloys but cobalt-chromium alloys, stainless steel, and others that have a surface layer of titanium or titanium alloys. Naturally, the implants made of titanium or titanium alloys need no such prior surface modification. The examples suitable for the biomedical implants include a series of metallic materials of titanium systems, that is, titanium and titanium alloys. The ingredient metals for the titanium alloys can be selected among such common metals as Al, Sn, Fe, Co, Ni, Cr, Cu, V, Mo, W, Ta, Ag, Zr, or other ones with considering mechanical properties, ease of shaping, or some other factors at manufacturing. Among the alloys, an alloy Ti—6Al—4V is appropriate. The biomedical implant materials should exhibit excellent biocompatibility and bioactivity by virtue of the hydrated surface oxide layer or hydrated gel layer that can spontaneously deposit apatite due to the calcium ions absorbed or involved inside.

Thus, the biomedical implant materials described in the present invention denote a group of solid materials for medical use consisting of the substances mentioned above, and no restriction is applied to shapes or usage as far as they ensures the properties necessary for the use in the human body, no harmfulness, or no toxicity. For example, plates, rods, blocks, sheets, fibers, pellets, or any other shapes will be suitable.

One of the most favorable solutions of calcium ions for the surface treatment of the substrates (implants) is an aqueous solution of calcium nitrate ($Ca(NO_3)_2$) with a concentration of 0.001 mol/L or more, and more concentrated one is appropriate for shorter periods of treatment. The less concentrated calcium nitrate solutions than that mentioned above can be effective as, well whereas a longer period of treatment is required. Room temperature is appropriate enough for the temperature of the solution for the electrochemical treatment, and temperatures above 0° C. will yield adequate results. Any solutions dissolved with calcium compounds other than calcium nitrate such as calcium chloride or calcium acetate can be employed for the electrochemical treatment.

The cathodic electrochemical treatment applied to the implant materials that are made of titanium or titanium alloys as well as those coated with a titanium or titanium alloy surface layer and have a hydrated oxide layer or a hydrated gel layer derived by a prior treatment with, for example, hydrogen peroxide solutions can also result in the same effects that are expected when it is applied to the implant materials treated with the anodic polarization: the calcium ions can be absorbed on or be involved in the hydrated oxide layer or a hydrated gel layer mentioned above.

Unless they are treated with the electrochemical polarization concerned with the present invention, neither of common titanium or titanium alloys nor any materials having titanium or titanium alloys as the surface layer have such an active hydrated titania gel, Therefore, instead of the hydrogen peroxide solution treatment, the anodic electrochemical treatment is to be so applied to those implant materials that the calcium ions can be more easily held on or in the surface hydrated titania gel layer, is, prior to the cathodic electrochemical surface treatment, the anodic electrochemical surface treatment is applied to the implant materials as they are kept in the same electrochemical cell so that such hydrated oxide layer or hydrated oxide gel layer can be yielded. With such consecutive and simple electrochemical treatments in the present invention, common titanium or titanium alloys or any materials having titanium or titanium alloys as the surface layer can hold calcium ions on or in the surface gel, hence the treatments can provide the materials with bioactivity superior to that derived from only a cathodic electrochemical treatment. Moreover, the present treatments alone result in much more excellent effects without help of a prior treatment with the hydrogen peroxide solutions.

Thus obtained biomedical implant materials covered with the hydrated oxide layer or hydrated oxide gel layer involving calcium ions exhibit prominent ability of spontaneously depositing apatite under body environment. The experiments with a simulated body fluid of the Kokubo recipe (SBF) have indicated that apatite is deposited within only 6 hours after soaking in SBF. Such excellent ability of in vitro depositing apatite definitely assures the implant materials of the superb in vivo biocompatibility and bioactivity, which has not been provided until the biocompatible biomedical implant materials are developed due to the electrochemical treatments in the present invention described above.

DETAILED DESCRIPTION OF THE PREFERRED EMBODIMENTS

The embodiments below will describe not only the surface treatment processes giving rise to the excellent biomedical implant materials but also the properties relevant to and characteristic of the present invention. The present invention, however, will not be restricted to the embodiments.

Titanium or titanium alloys were cut with a wire-discharge-cutter into specimens of 25×5×1 mm in size. They were ultrasonically washed beforehand with acetone to remove organics on the surface, followed by the chemical cleaning where the specimens were soaked in a 1 mass % aqueous solution of HF for 3 min and subsequently in a 1:1 mixture (in mass) of 1 mass % aqueous solution of HF and 3 mass % aqueous solution of $H_2O_2$ so that the surface oxide layer on the metal specimens was removed. The specimens were ultrasonically rinsed with distilled water for 5 min dried at 40° C. in an oven, and stored in close-capped polystryrene bottles until use.

Figure 1:
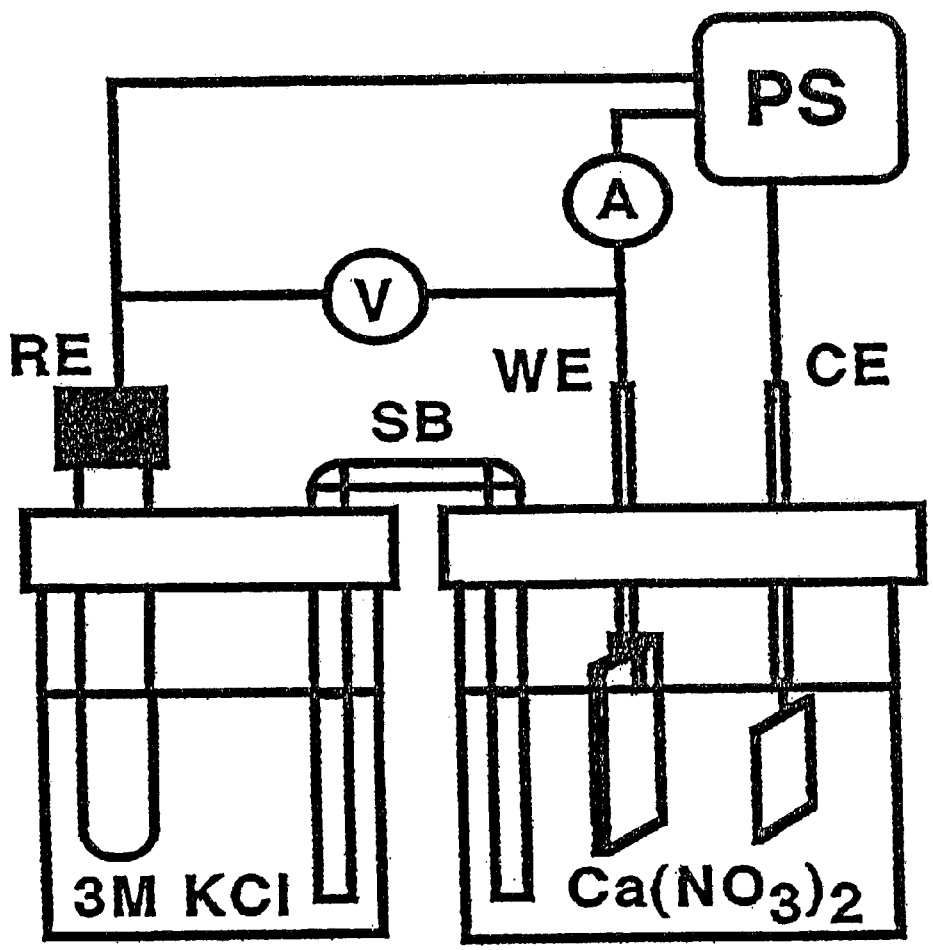
FIG. 1 is a schematic representation of the electrochemical cell.

FIG. 1 schematically illustrates the electrochemical cell employed for treating titanium or titanium alloy specimens in the present invention. PS in FIG. 1 denotes a potentiostat, WE denotes the working electrode, that is, the titanium or titanium alloy specimens prepared above. CE is the counter electrode, or a piece of Pt plate 25×5×1 mm in size, and RE denotes the Ag/AgCl reference electrode. RE was soaked in a 3 mol/L KCl aqueous solution held in the reference electrode cell (RE cell), while WE and CE were soaked in 0.01, 0.1, or 1 mol/L Ca(NO$_3$)$_2$ solutions held in the WE-CE cell. SB is the salt bridge electrochemically connecting the two cells, consisting of an inverted-U shaped glass pipe and agarose gel containing a 0.1 mol/L KCl aqueous solution.

With using thus prepared titanium specimen as WE, the surface treatments were conducted in the electrochemical cell illustrated by FIG. 1. When WE was subject to anodic polarization a hydrated oxide layer or hydrated oxide gel layer was yielded on the surface due to anodic oxidization. When WE was subject in turn to cathodic polarization, calcium ions were absorbed on the electrode surface. Thus, the anodic polarization of WE yields the hydrated oxide layer and the subsequent cathodic polarization results in the absorption of calcium ions on the surface.

With the titanium electrode as WE in the 0.1 mol/L Ca(NO$_3$)$_2$ electrolyte solution the potential was swept first from 0 V to −1.5 V, then up to +2.5 V, and subsequently down to 0 V at a rate of 0.02 V/s. A few peaks were found in the i-V curve at −1.1 V (A), −0.5 V (B), +0.9 V(C), and +1.8 V(D). Those on the anodic polarization can be attributed to changes in the oxidation state of titanium: (C) and (D) are concerned with TiO$_2$.2H$_2$O and TiO$_3$.2H$_2$O while the peaks on the cathodic polarization are relevant to the appearance of Ti(OH)$_3$ (A) and TiO (B) due to reduction of the surface oxide.

With reducing the concentration of the Ca(NO$_3$)$_2$) aqueous electrolyte solution the i-V curve showed a peak was observed at +1.8 V (WE=Ti) corresponding to gas evolution at both electrodes. This indicated electrolysis of water, and hydrogen (H$_2$) was evolved at the cathode (Pt=CE) and oxygen (O$_2$) was at the anode (WE=Ti). The, anodic current is controlled by two factors: one is the anodic oxidation and dissolution of titanium electrode, and the other is electrolysis of water accompanied by rigorous stirring effects due to gas evolution. With the electrochemical treatments in the present invention re-dox reactions take place more or less on the surface of titanium or titanium alloy electrodes, and they control the bioactivity of the implant materials.

The ability of depositing apatite has been evaluated for the titanium metal substrate specimens after the consecutive electrochemical treatments in the following way. The specimens were taken out from the electrochemical cell, rinsed with distilled water, and dried for 24 hours at room temperature. Then they were soaked for 3 hours, 6 hours, 12 hours, 1 day and 3 days in SBF (pH=7.4) whose composition was shown in Table 1, before the TF-XRD patterns were recorded and SEM photographs were taken to examine the deposition of apatite.

TABLE 1

| ions | concentration (×10$^{-3}$ M) |
|---|---|
| Na$^+$ | 142.0 |
| K$^+$ | 5.0 |
| Ca$^{2+}$ | 2.5 |
| Mg$^{2+}$ | 1.5 |
| Cl$^-$ | 147.8 |
| HCO$_3^-$ | 4.2 |
| HPO$_4^{2-}$ | 1.0 |
| SO$_4^{2-}$ | 0.5 |

Figure 2A:
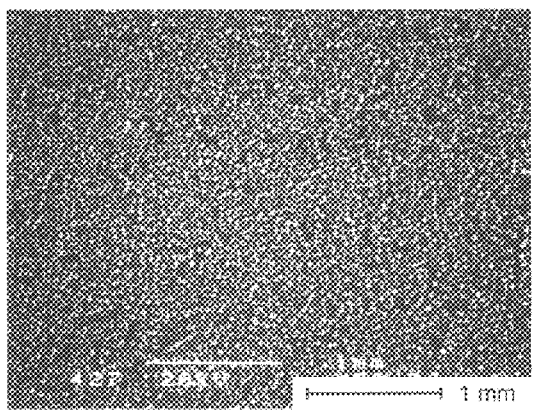
FIG. 2 shows scanning electron micrographs (SEM photographs) of the electrochemically treated metallic titanium substrates before soaking in SBF; (a) is for a specimen after the anodic and cathodic treatments at +9.5 V and −2.0 V, respectively, and (b) is for a specimen with only cathodic treatment.
Figure 2B:
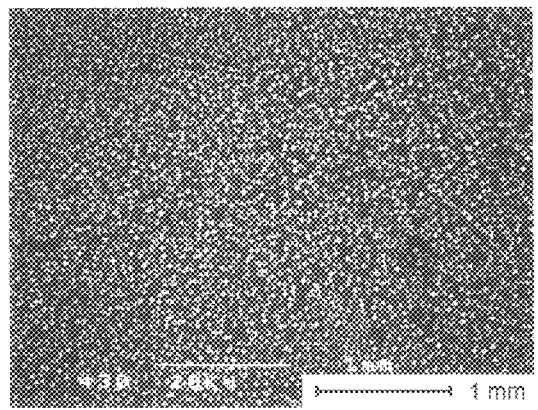
Figure 3C:
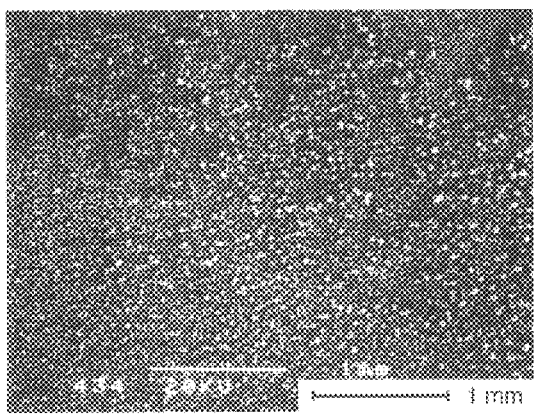
FIG. 3 shows SEM photographs of the titanium substrates after soaked in SBF for 3 days: (c) and (d) were subject to the same treatments as (a) and (b), respectively.
Figure 3D:
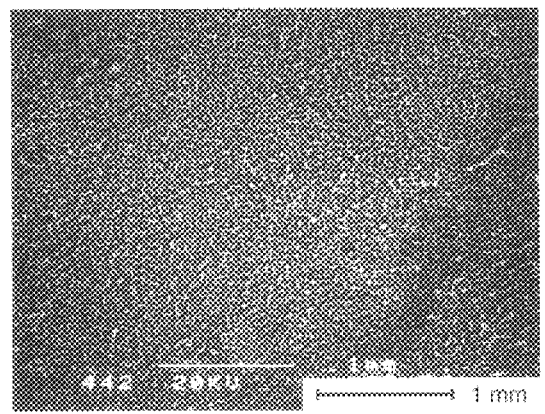
Figure 4E:
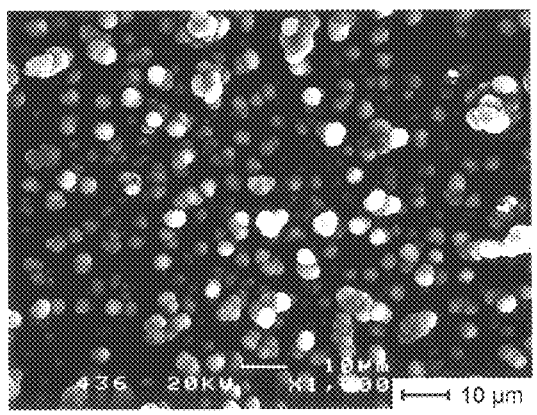
FIG. 4 shows SEM photographs with a larger magnification than those in FIG. 3 of the titanium substrates after soaked in SBF for 3 days: (e) and (f) were subject to the same treatments as (a) or (c), and (b) or (d), respectively.
Figure 4F:
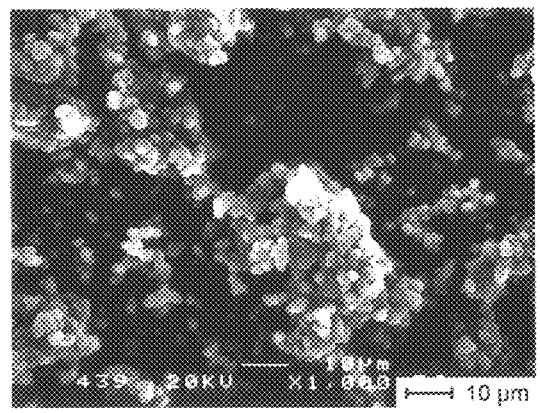

A anodic electrochemical treatment at a potential less than +1.5 V alone failed to provide the titanium substrate with the bioactivity since the substrate could not deposit apatite when soaked in SBF up to 14 days. This may be attributed either to appearance of a thinner layer on the substrate surface or to absorption of only trace amount of calcium ions. Thus not only a greater anodic potential was applied to the titanium substrate (WE) so as to yield a thicker gel surface layer or a cathodic polarization treatment but the consecutive treatments of anodic and cathodic polarizations were also applied. FIGS. 2 through 4 are SEM photographs of the titanium substrate before soaking in SBF or the substrate after soaking in SBF for 3 days. Among those photographs, (a), (c), and (e) are for the titanium specimen (WE) treated electrochemically at +9.5 V for 1 hour and subsequently at −2.0 V for 10 min taking a 0.1 mol/L Ca(NO$_3$)$_2$ aqueous solution as the electrolyte solution in the WE-CE cell, while (b), (d), and (f) show surface structures of the titanium (WE) only treated at −2.0 V for 10 min.

FIG. 2 indicates rough surface structures of both specimen (a) and (b) before soaking in SBF. Specimen (a) had a blue-purplish tint on the surface before soaking. FIGS. 3 (c) and (d) for the specimen after soaking in SBF indicate brighter and darker area. FIGS. 4 (e) and (f) are the photographs with a greater magnification for (c) and (d), respectively.

FIGS. 4 (e) and (f) show spherical agglomerates of apatite, similar in shape to those found on bioactive materials after soaking in SBF. The TF-XRD patterns of the specimens confirmed that they were apatite.

Figure 5:
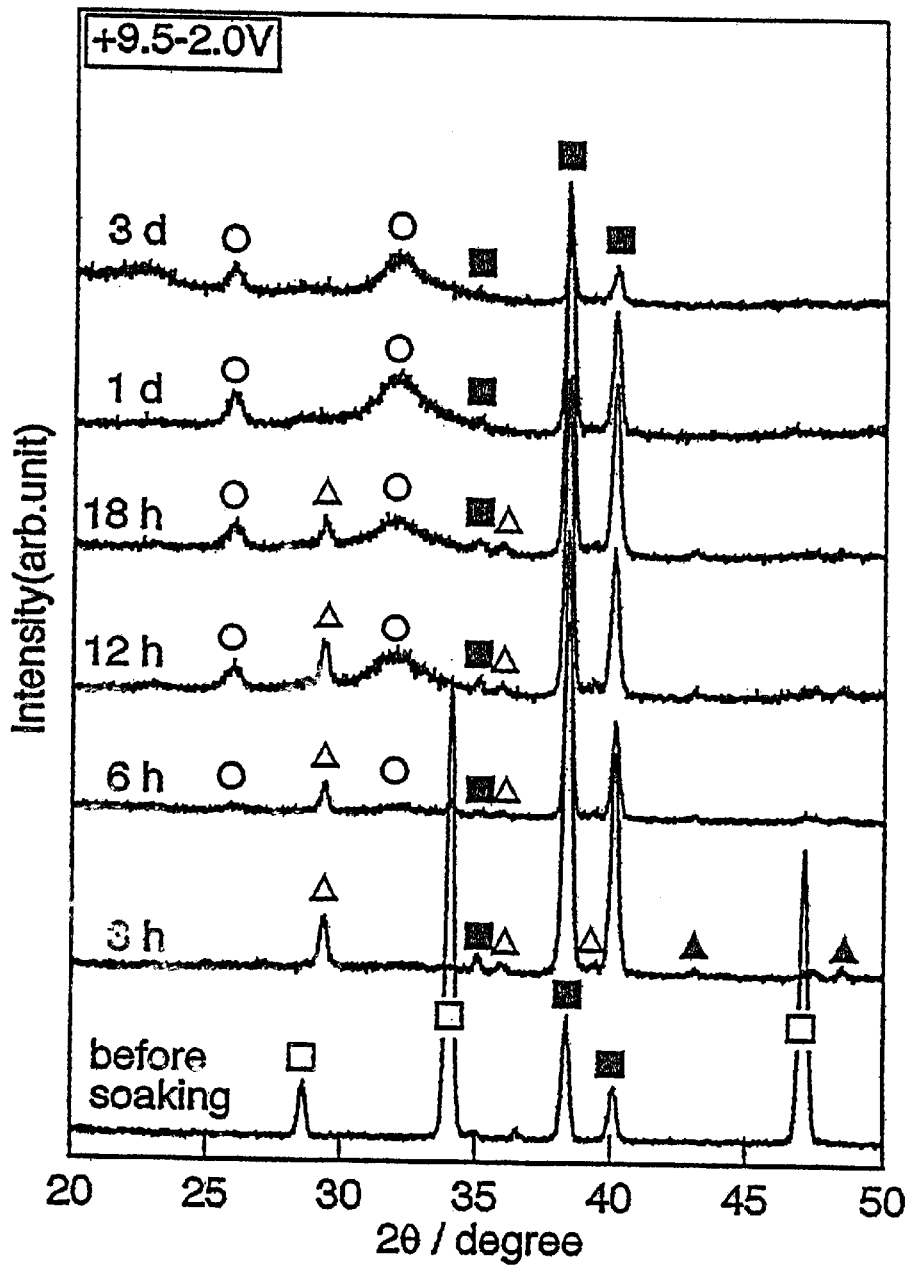
FIG. 5 shows Cu Kα thin film X-ray diffraction (TF-XRD) patterns for the titanium substrates with the anodic and cathodic electrochemical treatments, and indicates their ability of apatite deposition.
Figure 6:
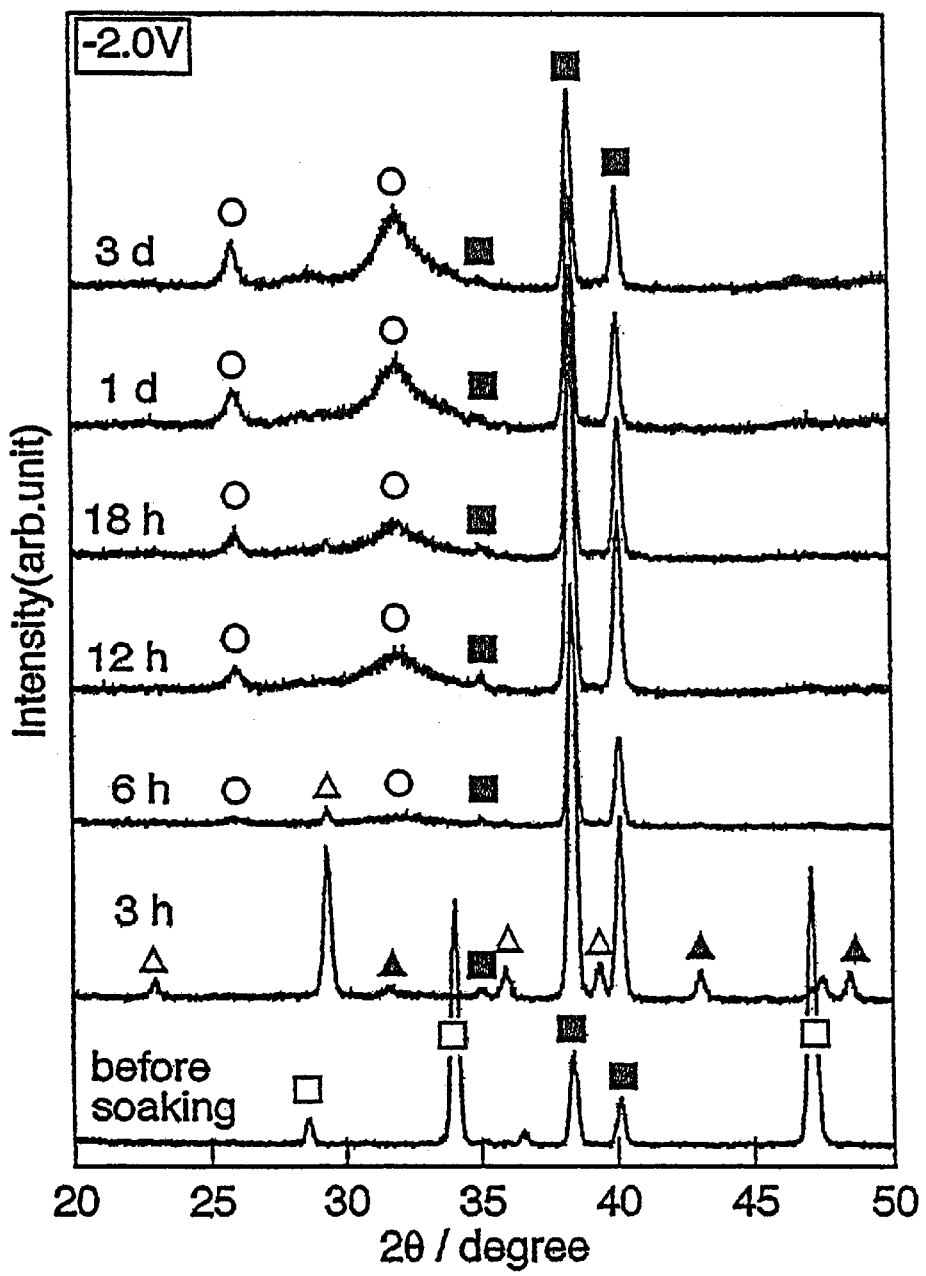
FIG. 6 shows the TFXRD patterns of the titanium substrates electrochemically treated only with a cathodic polarization at −2.0 V.

FIGS. 5 and 6 represent the TF-XRD patterns of specimens (a) (c) (e) and (b) (d) (f), respectively. The diffractions of apatite denoted by open circles were detected at about 26 and 32 in 2θ for the specimens after soaking in SBF for 3 days. Specimen (a) denoted as +9.5−2.0V and (b) denoted as −2.0V could not show the apatite diffractions (open circles) after soaking for 0 hour and 3 hours, while such diffraction peaks were detected after 6 hours soaking for specimen (a) and (b). FIGS. 5 and 6 also indicate a strong peak denoted by open square due to calcium hydroxide for the as-treated specimens (denoted as "before soaking"), while another peaks (denoted by closed and open triangle) grew at the expense of the calcium hydroxide peak as the specimens were soaked in SBF. They were due to hexagonal and rhombohedral calcium carbonates (vaterite and calcite, respectively). This suggests that calcium hydroxide produced at the electrochemical treatments was reacted with HCO$_3^-$ ions in SBF to yield calcium carbonate. It is thus obviously indicated that the hydrated oxide or hydrated gel layer involving calcium hydroxide is produced by the electrochemical treatments.

A comparison between FIG. 5 and FIG. 6 indicates that both specimens, +9.5−2.0V and −2.0V, gave calcium hydroxide diffraction peaks with similar intensity, and both deposited apatite after soaking in SBF for 6 hours. However, the apatite layer deposited on the former specimen was more strongly fixed to the substrate while that on the latter one tended to show weaker fixation.

Then, a titanium specimen was subject to a prior chemical treatment with a hydrogenperoxide solution containing Ta(V) before it was subsequently subject to the cathodic electrochemical treatment at −2.0 V. The chemical treatment was applied to the specimen by soaking in a 30 mass % hydrogenperoxide aqueous solution containing 5 mmol/L $TaCl_5$ at 60° C. for 24 hours, rinsing, and drying at room temperature. Thus obtained samples deposited an apatite layer as did specimen +9.5–2.0V.

With applying the cathodic electrochemical treatment alone to biomedical implant materials having titanium or titanium alloys on their surface, a hydrated oxide layer or hydrated oxide gel layer involving $Ti(OH)_3$ or $TiO_2$, though not identifiable yet, was yielded, and the layer was indicated to favor the deposition of apatite active in body environments. Moreover, application of the anodic electrochemical treatment prior to the cathodic one not only yielded a hydrated oxide or gel layer of $TiO_2.2H_2O$ or $TiO_3.2H_2O$ that was fixed strongly to the substrate but also gave rise to better ability of depositing apatite. Similar effects were confirmed for the specimen treated chemically with the hydrogenperoxide solution before the cathodic electrochemical treatment. Therefore, the formation of such hydrated oxide layer or hydrated oxide gel layer resulted in earlier deposition of apatite or fixation to living tissue when implanted. Thus the present invention, that is, simple electrochemical treatments at room temperature could alone produce the biomedical implant materials with excellent biocompatibility.

We claim:

1. A biocompatible implant for medical use comprising:
    an implant having a surface layer of hydrated titanium oxide on a surface of a titanium or titanium alloy; and
    calcium ions held on said surface layer of said hydrated titanium oxide on said surface of titanium or titanium alloy by:
        treating said implant electrochemically in an electrolyte solution containing calcium ions using said implant as an anode to thereby form said layer of hydrated titanium oxides on said surface of said titanium or titanium alloy of said implant; and
        electrochemically treating said implant in an electrolyte solution containing calcium ions with said implant being used as a cathode.

2. A biocompatible implant according to claim 1 wherein said electrolyte solution comprises a calcium nitrate solution.

3. A biocompatible implant for medical use comprising:
    an implant having a surface layer of hydrated titanium oxide on a surface of a titanium or titanium alloy; and
    calcium ions held on said layer of hydrated titanium oxide on said surface of said titanium or titanium alloy by electrochemically treating said implant in an electrolyte solution containing calcium ions with said implant being used as a cathode.

4. The biocompatible implant for medical use according to claim 3, wherein said layer of hydrated titanium oxide is formed by treating said implant electrochemically in an electrolyte solution containing calcium ions using said implant as an anode to thereby for a layer of hydrated titanium oxides on said surface of said titanium or titanium alloy of said implant.

5. A biocompatible implant for medical use according to claim 3, wherein before said implant is used as cathode, said implant is applied with a prior treatment of:
    treating said surface of said implant chemically with hydrogen peroxide solutions to thereby form a layer of hydrated titanium oxides on said surface of said titanium or titanium alloy.

* * * * *